United States Patent [19]

Anderson

[11] 4,223,677
[45] Sep. 23, 1980

[54] ABSORBENT FIBROUS STRUCTURE AND DISPOSABLE DIAPER INCLUDING SAME

[75] Inventor: James E. Anderson, Moorestown, N.J.

[73] Assignee: Scott Paper Company, Philadelphia, Pa.

[21] Appl. No.: 38,341

[22] Filed: May 11, 1979

Related U.S. Application Data

[63] Continuation of Ser. No. 753,675, Dec. 23, 1976, abandoned.

[51] Int. Cl.$^3$ .............................................. A61F 13/16
[52] U.S. Cl. ................................. 128/287; 128/290 P
[58] Field of Search ................... 128/284, 287, 290 R, 128/290 B, 290 P, 296, 285, 155, 156

[56] References Cited

U.S. PATENT DOCUMENTS

| | | | |
|---|---|---|---|
| 2,486,805 | 11/1949 | Seymour et al. | 128/284 |
| 2,488,700 | 11/1949 | Bidwell | 92/44 |
| 2,622,308 | 12/1952 | Harris et al. | 19/145.5 |
| 2,881,669 | 4/1959 | Thomas et al. | 92/39 |
| 2,931,749 | 4/1960 | Kine et al. | 428/290 |
| 3,105,491 | 10/1963 | Harwood | 128/290 R |
| 3,206,351 | 9/1965 | Smith | 428/113 |
| 3,336,182 | 8/1967 | Bassett et al. | 428/288 |
| 3,512,218 | 5/1970 | Langdon | 19/156.3 |
| 3,740,797 | 7/1973 | Farrington | 19/156.3 |
| 3,768,118 | 10/1973 | Ruffo et al. | 19/156.3 |
| 3,768,480 | 10/1973 | Mesek et al. | 128/287 |
| 3,777,758 | 12/1973 | Mesek et al. | 128/284 |
| 3,952,124 | 4/1976 | Mesek | 428/290 |
| 4,045,833 | 9/1977 | Mesek et al. | 128/287 |

OTHER PUBLICATIONS

Skiest, Irving, Handbook of Adhesives, 1962, Reinhold Publishing Corp., Chapt. 58, pp. 647-661.

Primary Examiner—Robert W. Michell
Assistant Examiner—C. W. Shedd
Attorney, Agent, or Firm—Martin L. Faigus; William J. Foley

[57] ABSTRACT

An absorbent fibrous structure includes intermingled absorbent fibers of a varying length up to about 6.35 mm. These absorbent fibers are graded by length through the thickness of the structure so that long length absorbent fibers are more concentrated than shorter length absorbent fibers at a first surface of the structure, and the shorter length fibers are more concentrated than the longer length fibers at an opposing second surface of the structure. The grading of absorbent fibers by length provides a capillary gradient through the thickness of the absorbent structure wherein capillary pores are graded by size so that large capillary pores are more concentrated than small capillary pores at the first surface of the absorbent structure, and smaller capillary pores are more concentrated than larger capillary pores at the opposing second surface of the structure.

The absorbent fibrous structure of this invention may be employed as an absorbent core of an improved disposable diaper. The core is disposed between a liquid-pervious facing sheet and a backing sheet so that the long length absorbent fibers are more concentrated than the shorter length fibers at the surface of the core closest the facing sheet, and the shorter length fibers are more concentrated than the longer length fibers at the surface of the core closest the backing sheet. Absorbent fibrous structures made according to this invention may also be suitably treated with adhesive or other materials, such as plastic, and employed as absorbent wipers, incontinent pads, and the like.

10 Claims, 5 Drawing Figures

ABSORBENT FIBROUS STRUCTURE AND DISPOSABLE DIAPER INCLUDING SAME

This is a continuation of application Ser. No. 753,675 filed Dec. 23, 1976, now abandoned.

BACKGROUND OF THE INVENTION

1. Field of the Invention

This invention relates generally to absorbent fibrous structures, and more particularly to articles, such as disposable diapers, including the fibrous structures as absorbent structures thereof. In disposable diapers, the fibrous structure is employed as an internal component that preferentially directs body liquids through its thickness and away from the facing sheet.

2. Description of the Prior Art

Disposable diapers having an absorbent component disposed between a facing sheet and a backing sheet have become popular in recent years because of their relatively low cost which permits them to be economically disposed of after a single use. In designing such diapers, it is extremely important to effectively utilize the absorbent capacity of the diaper to retain discharged body liquids such as urine, and to prevent such liquids from leaking from the internal absorbent components through the facing sheet contacting the wearer (wetback). If the absorbent capacity of the diaper is not effectively utilized, or is inadequate, premature leakage of body liquids can occur. If the diaper is not properly designed to inhibit the wetback of body liquids the surface of the diaper touching the wearer's skin may become excessively wet; causing chafing and/or rash formation.

U.S. Pat. No. 3,768,480, issued to Mesek et al, is directed to a disposable diaper having a facing sheet designed for the purpose of promoting the penetration of urine through the facing sheet and into an internal absorbent batt. The promotion of urine through the facing sheet is achieved by providing a gradually increasing wettability gradient within the facing sheet. The wettability gradient is formed by intermingling one type of absorbent fibers with another type of fibers that are less wettable, and establishing an increasing concentration gradient through the thickness of the sheet for the more wettable fibers. The facing sheet is a blend of long fibers having a length greater than about 6.35 mm and short fibers having a length less than about 6.35 mm, with the short fibers being more wettable than the long fibers. The concentration of short fibers gradually increases from the surface of the facing sheet adjacent the wearer to the surface adjacent the absorbent batt. The facing sheet can be formed in accordance with the method and apparatus disclosed in U.S. Pat. No. 3,768,118, issued to Ruffo et al. The concentration gradient of short fibers imparts an increasing wettability gradient to the facing sheet, and this wettability gradient promotes the flow of urine through the facing sheet and toward the internal absorbent batt. The loosely compacted absorbent batt is constructed to be more wettable than the facing sheet to aid in drawing urine from the facing sheet into the batt. Further, after it has been initially formed, the structure of the absorbent batt is modified to encourage the effective utilization of the absorbent area of the batt to prevent localized flooding therein and undesirable wetback therefrom. As a result of the abovedescribed construction, urine is preferentially directed through the facing sheet and into the absorbent batt.

The absorbent batt disclosed in the '480 patent is modified, after its formation, by providing a paper-like densified wicking layer on one surface thereof in accordance with the processes described in U.S. Pat. No. 3,017,304 and in the '480 patent to Mesek et al. Specifically, the wicking layer is formed in situ by applying moisture to one surface of the batt, and thereafter applying pressure to the batt to densify the moistened surface. The wicking layer provides a modified capillary structure in selected regions of the absorbent batt for the purpose of promoting the desired distribution of urine.

Although the posttreating of an absorbent batt for the purpose of providing a wicking layer therein may improve the fluid distributing properties of said batt, it is believed to be desirable to initially form the absorbent batt with a capillary structure that promotes effective utilization of its absorbent capacity and aids in preventing wetback.

SUMMARY OF THE INVENTION

The absorbent structure of this invention includes intermingled absorbent fibers of a varying length up to about 6.35 mm. The absorbent fibers are graded by length through the thickness of the structure so that long length absorbent fibers are more concentrated than shorter length fibers at a first surface of the structure and shorter length absorbent fibers are more concentrated than longer length fibers at an opposing second surface of the structure. This unique construction provides a capillary gradient through the thickness of the absorbent structure wherein capillary pores are graded by size so that large capillary pores are more concentrated than small capillary pores at the first surface of the absorbent structure, and smaller capillary pores are more concentrated than larger capillary pores at the opposing second surface of the structure. The capillary gradient preferentially directs liquids through the thickness of the structure from the first to the second surface.

The improved disposable diaper of this invention has an absorbent core including the absorbent fibrous structure of this invention. The core is disposed between a liquid-pervious facing sheet and a backing sheet which preferably is liquid-impervious. The absorbent fibers of the core are graded by length through the thickness of the core so that longer length absorbent fibers are more concentrated than shorter length absorbent fibers at the surface of the core closest the facing sheet, and the shorter length absorbent fibers are more concentrated than the longer length absorbent fibers at the surface of the core closest the backing sheet. This unique arrangement of absorbent fibers provides a capillary gradient through the absorbent core wherein the smallest capillary pores are located at the surface of the core closest the backing sheet and the largest capillary pores are located at the surface of the core adjacent the facing sheet. This size distribution of capillary pores preferentially directs the urine through the thickness of the core, away from the facing sheet, and toward the backing sheet. Further, as the urine is preferentially directed through the thickness of the core it is also directed laterally to provide for effective utilization of the absorbent capacity of the core. Moreover, the capillary structure in the absorbent core tends to inhibit the wetback of urine into the facing sheet since the urine tends to flow toward the smaller pores of the core. Inhibiting wetback of urine into the facing sheet aids in maintaining the facing sheet in a relatively dry condition. By maintaining a relatively dry condition against the skin of a wearer undesirable chafing and/or rash formation is minimized.

Although the absorbent core of the disposable diaper of this invention provides for improved utilization of absorbent capacity, as compared to prior art absorbent core structures, it is within the scope of this invention to provide a wicking layer adjacent a lower surface of the core to further improve the liquid handling capabilities of the diaper. This wicking layer can be a separate sheet having a greater density, and smaller pore size, than the surface of the absorbent core against which it is positioned. Alternatively, the wicking layer can be a paper-like densified layer formed in situ with the absorbent core in accordance with the method disclosed in U.S. Pat. No. 3,017,304, referred to earlier in this application. It may be most desirable to employ a wicking layer for use in those situations where large quantities of body liquids are required to be absorbed, as for example, in an overnight diaper, or a diaper for large children or incontinent adults.

Although the absorbent structure of this invention has been found to be particularly suitable for use as an internal absorbent element of a disposable diaper, it may also be used in other applications where it is desired to preferentially direct absorbed liquids away from a specific area. For example, the absorbent structure may be employed as an absorbent wiper when the structure has been suitably treated to enhance its structural integrity and abrasion resistance. One means of so treating the structure is to apply adhesive either continuously or in suitable patterns to one or both surfaces of the web by well known methods, such as spraying or print bonding. Further, two or more absorbent structures made according to this invention may be appropriately arranged into novel absorbent articles. For example, two absorbent structures of this invention may have their first surfaces juxtaposed to provide an absorbent wiper having excellent absorbency and wipe dry characteristics on both of its major surfaces. Alternatively, two absorbent structures of this invention may have their second surfaces juxtaposed to provide a wiper or other absorbent article in which liquid is preferentially directed into the interior of the article from both of its major surfaces.

Other objects and advantages of this invention will become apparent by referring to the detailed description which follows, taken in conjunction with the drawings.

DESCRIPTION OF THE PREFERRED EMBODIMENTS

For purposes of illustration, the absorbent fibrous structure of this invention will be described in terms of its employment as an internal absorbent core of a disposable diaper. However, it is to be understood that the absorbent structure of this invention is not limited to such use. For example, the absorbent structure may be employed as an absorbent wiper after the structure has been suitably treated with an adhesive or other material to enhance its structural integrity and abrasion resistance. Further, the absorbent structure may be used as an absorbent member in surgical dressings, incontinent pads, bed pads and other articles designed to absorb body liquids. However, the absorbent structure of this invention has been found to be particularly suitable for use as an absorbent core of a disposable diaper. Thus, the following description of the absorbent core and its manner of formation applies equally to the absorbent structure of this invention.

Figure 1:
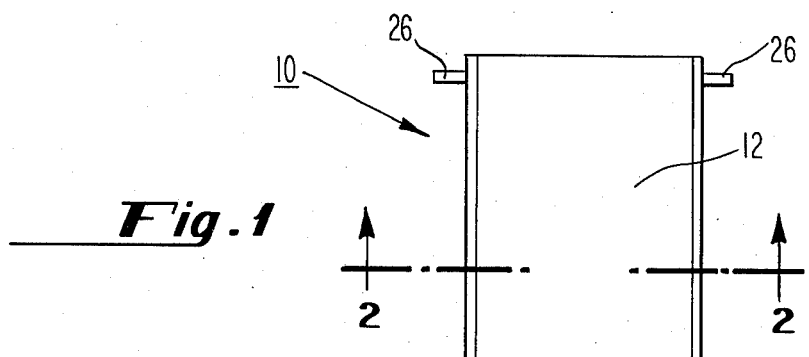
FIG. 1 is a plan view of a disposable diaper of this invention.
Figure 2:
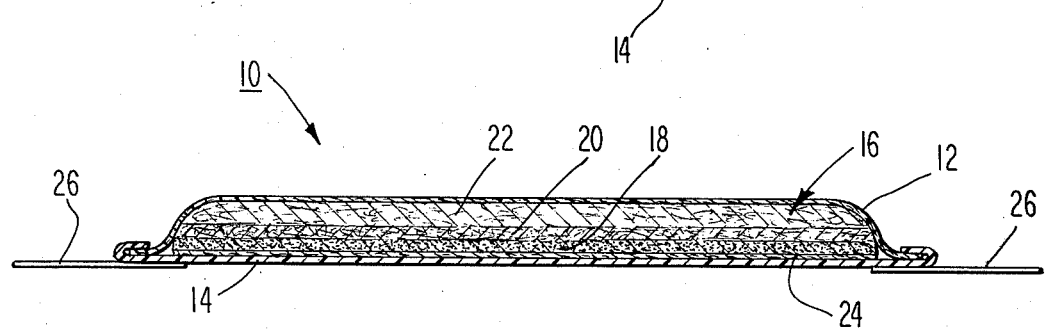
FIG. 2 is a cross-sectional view along line 2—2 of FIG. 1 showing details of an absorbent fibrous structure of this invention.

Referring to FIGS. 1 and 2, a disposable diaper 10 of this invention includes a liquid-pervious facing sheet 12, a backing sheet 14 which is preferably liquid-impervious, and an absorbent fibrous core 16 disposed between the backing and facing sheets. The absorbent core 16 includes intermingled absorbent fibers of a varying length up to about 6.35 mm. The absorbent fibers are preferably loosely compacted and are graded by length through the thickness of absorbent core 16 so that long length absorbent fibers are more concentrated than shorter length absorbent fibers at the surface of the core closest facing sheet 12, and the shorter length absorbent fibers are more concentrated than the longer length absorbent fibers at the surface of the core closest backing sheet 14.

In one embodiment of this invention, absorbent core 16 may be comprised of a single continuously made web or batt of absorbent fibers graded through the thickness of the core as described in the preceding paragraph. In another embodiment, the core 16 may comprise an assemblage of a plurality of layers of absorbent fibers, with each layer being classified so that it contains absorbent fibers of a specific weighted average fiber length. The layers are assembled so that the overall grading of absorbent fibers in the core 16 corresponds to the grading of absorbent fibers as described herein above. In other words, the classified layer of absorbent fibers closest the facing sheet 12 has a greater concentration of long length absorbent fibers than any other classified layer in the absorbent core, and the concentration of the long length absorbent fibers decreases from layer to layer as one moves through the core to the classified layer closest the backing sheet 14. Thus, for both the continuously formed absorbent core and the core formed of assembled classified layers, the concentration of long length absorbent fibers decreases and the concentration of short length absorbent fibers increases through the thickness of the core in a direction from the facing sheet 12 to the backing sheet 14. The number of classified layers of absorbent fibers employed to form an absorbent core is a matter of choice. For purposes of description, absorbent core 16 is shown in FIG. 2 as including three of such classified layers; an upper layer 22, a middle layer 20 and a lower layer 18.

The unique arrangement of absorbent fibers within the absorbent core 16 provides for effective utilization of the absorbent capacity of the core. The arrangement of absorbent fibers provides a capillary gradient through the absorbent core 16 with the smallest capillary pores at the surface of the core closest the backing sheet 14 and the largest capillary pores at the surface of the core adjacent the facing sheet 12. This distribution of capillary pore size preferentially directs liquids, such as urine, through the thickness of the core 16 towards the backing sheet 14 and away from the facing sheet 12. Further, the distribution of capillary pore size also directs urine laterally in the core to provide for effective utilization of the absorbent capacity of the core. The lateral directing of urine is greatest in the area of the core 16 having the smallest capillary pores. Thus, urine entering core 16 is increasingly directed laterally as it is directed through the core towards the backing sheet 12. The increasing lateral spreading and preferential direction through the core 16 towards the backing sheet 14 prevents localized flooding and tends to inhibit the wetback of urine into the facing sheet. Inhibiting wetback of urine aids in maintaining the facing sheet in a relatively dry condition against the skin of the wearer and thereby minimizes undesirable chafing and/or rash formation.

Figure 3:
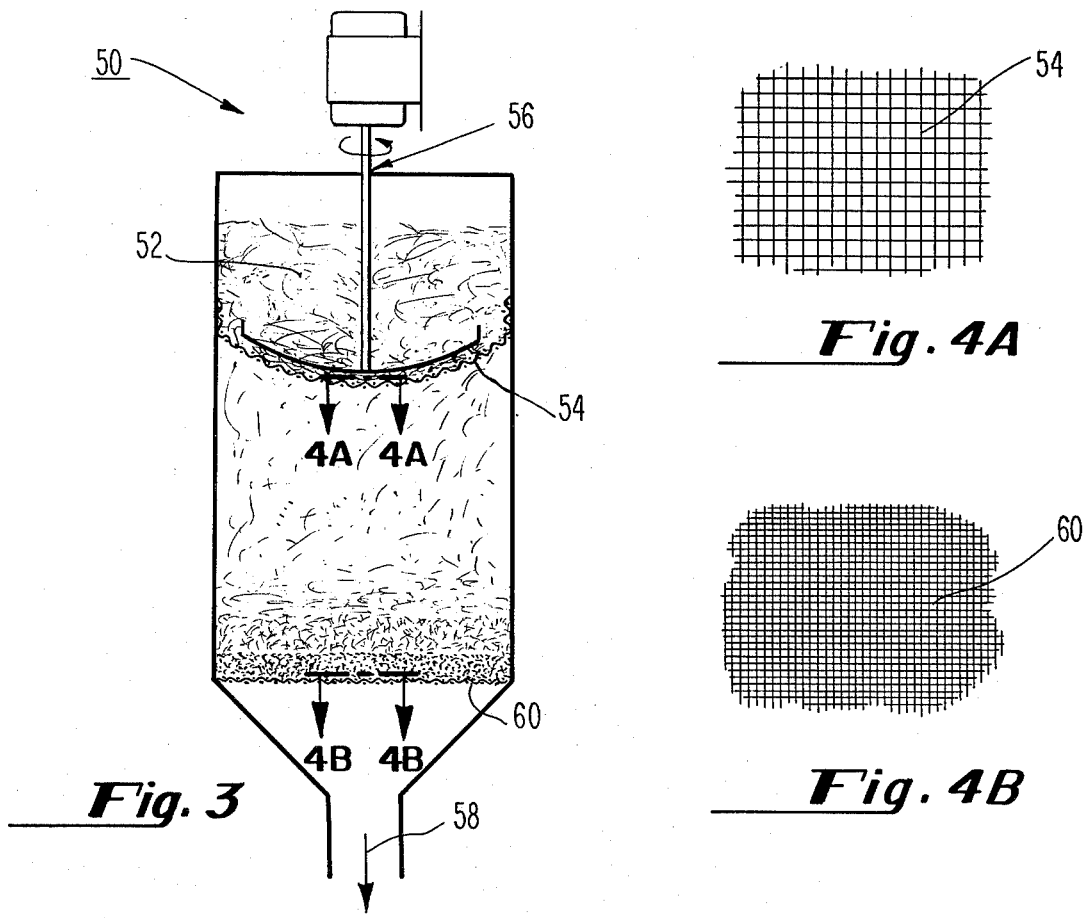
FIG. 3 is a schematic cross-sectional view taken along the longitudinal axis of a batt former used to make the fibrous structure of this invention.
Figure 4A:
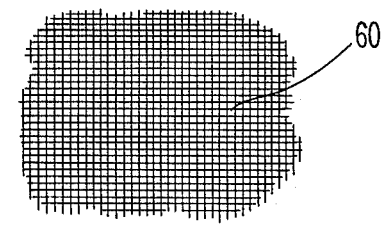
FIGS. 4A and 4B are fragmentary sectional views of the screens of the batt former taken along lines 4A—4A and 4B—4B, respectively of FIG. 3, and illustrating the relative mesh sizes of the screens.
Figure 4B:
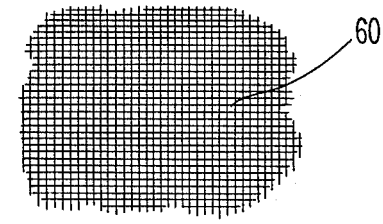

Referring to FIG. 3, an absorbent core 16 of this invention can be constructed in a laboratory with batt forming device 50. A sample cores 16 was continuously formed in batt former 50 by adding 25 grams of fiberized wood pulp fibers 52 to a 10×10 mesh basket 54 in the batt former. A motorized scraper 56 in basket 54 keeps the fibers 52 from clogging the pores in the basket until they are pulled through the screen of the basket 54 by an air flow moving in the direction indicated by arrow 58. The air flow pulls fibers 52 through the screen of basket 54 towards a 100 mesh wire screen 60 where they are collected. The first fibers 52 through basket 54 have the shortest weighted average fiber length. As fibers 52 are continuously pulled through basket 54, the average length of the fibers increases with the last fibers pulled through the basket having the longest average fiber length. In this specification and claims, average fiber length refers to weighted average fiber length.

To analyze the length of the fibers in the absorbent core 16, 25 grams of Southern pine pulp lap were fiberized, added to the batt former 50, and collected on the 100 mesh screen 60 as discrete first, second and third samples each having equal weight. The weighted average fiber length of each sample was then determined in accordance with official standard no. T233os-75 of the Technical Association of the Pulp and Paper Industry (TAPPI) by running each sample through a four screen Bauer-McNett type classifier which separated each sample into five fractions that were classified by fiber length. Each screen collected one fraction and the fifth fraction was the remainder of fibers in the sample that passed through all the screens. The openings in the screens of the Bauer-McNett classifier were: 14 mesh (1.19 mm); 28 mesh (0.595 mm); 48 mesh (0.297 mm) and 100 mesh (0.149 mm).

The weighted average fiber length for the first, second and third samples as measured by fiber length was 1.34 mm, 2.02 mm and 2.33 mm, respectively.

Although a preferred embodiment of the disposable diaper of this invention has been described it is also within the scope of this invention to include a wicking layer 24 disposed between core 16 and backing sheet 14. The wicking layer 24 can be a separate sheet having preferably a greater density and smaller capillary pore size than the surface of the absorbent core 16 against which it is positioned. Alternatively, wicking layer 24 can be in the form of a paper-like densified layer of the absorbent core 16 that is formed in situ in accordance with the method disclosed in U.S. Pat. No. 3,017,304. It may be desirable to employ wicking layer 24 for use in those situations where large quantities of liquids are required to be absorbed, as for example, in an overnight diaper, or a diaper for large children or incontinent adults.

Diaper closure tabs 26 are preferably included with the diaper 10 to secure it to a wearer.

It is also within the scope of this invention to include textile length fibers, that is, fibers having a length greater than 6.35 mm, in absorbent core 16 to impart strength and stability to the core. The textile length fibers are preferably uniformly concentrated through the core 16. When applicant refers to grading of an absorbent fiber in core 16 or in the absorbent structure of this invention, applicant refers to the grading of fibers having a length less than about 6.35 mm. However, textile length fibers included in the core can be graded or not graded as desired.

Although illustrated as the absorbent core 16 of the disposable diaper 10, the absorbent structure of this invention may also be employed as an absorbent wiper after the structure has been suitably treated to enhance its mechanical integrity and abrasion resistance. One means of treating the structure is to apply adhesive to the opposed surfaces of the structure by well known methods, such as spraying, thermal bonding, or print bonding. The appropriate amount of adhesive applied to each surface is dictated by the characteristics desired in the web and can readily be determined by one of ordinary skill in the art. In some situations it may be preferable to form a liquid-impervious adhesive skin on the second surface of the absorbent structure, that is, on the surface having the greatest concentration of short length absorbent fibers. The wiper so formed may be especially desirable for wiping up particularly disagreeable substances which desirably should be isolated from the hands of the user. The structure can also be treated by adhering a liquid-impervious film or plastic sheet to the second surface. Further, two or more absorbent structures made according to this invention may be appropriately arranged into novel absorbent articles. For example, two absorbent structures of this invention may have their first surfaces juxtaposed to provide an absorbent wiper having excellent absorbency and wipe dry characteristics on both of its major surfaces. Alternatively, two absorbent structures of this invention may have their second surfaces juxtaposed to provide a wiper or other absorbent article in which liquid is preferentially directed into the interior of the article from both of its major surfaces. Further, two or more absorbent structures of this invention may be laminated together to provide an absorbent article having increased absorbent capacity. The foregoing examples are intended to describe rather than limit the numerous absorbent articles which can be made by arranging two or more absorbent structures of this invention. It is also within the scope of this invention to include textile length fibers in the absorbent structures of this invention to impart additional strength and structural integrity thereto.

Having described my invention I claim:

1. An absorbent, dry-formed structure including one type of cellulosic fibers having a varying length no greater than about 6.35 mm., said cellulosic fibers being disposed in at least three different classified layers and having a different weighted average fiber length in each of said layers; said layers being superimposed upon each other in said absorbent structure so that the weighted average fiber length of said cellulosic fibers decreases from layer to layer in a direction from one outer surface to the opposed outer surface.

2. The absorbent structure of claim 1, wherein the one type of cellulosic fibers is wood pulp.

3. An absorbent wiper comprising the absorbent structure of claim 1, said structure having adhesive disposed on at least one of its outer surfaces.

4. The absorbent wiper of claim 3 wherein adhesive is disposed upon both outer surfaces.

5. The absorbent wiper of claim 4 wherein the adhesive on one outer surface forms a liquid impervious skin.

6. A disposible diaper comprising an absorbent core disposed between a liquid-impervious backing sheet and a liquid-pervious facing sheet, the improvement wherein said absorbent core includes a loosely compacted, dry-formed batt having one type of cellulosic fibers of a varying length no greater than about 6.35 mm., said cellulosic fibers being intermingled with each other and being classified by weighted average fiber length throughout the thickness of the batt so that the weighted average fiber length of the cellulosic fibers at the surface of the batt closest the facing sheet is greater than the weighted average fiber length of the cellulosic fibers at the surface of the batt closest the backing sheet, said batt including an interior region wherein the weighted average fiber length of the cellulosic fibers is less than the weighted average fiber length at the surface of the batt closest the facing sheet and greater than the weighted fiber length at the surface of the batt closest the backing sheet.

7. The disposable diaper of claim 6 wherein the one type of cellulosic fibers is disposed in at least three different classified layers and has a different weighted average fiber length in each of said layers, said layers being superimposed upon each other to establish the gradation in weighted average fiber length through the thickness of the batt.

8. The disposable diaper of claim 7 wherein the one type of cellulosic fibers is wood pulp.

9. The disposable diaper of claim 8 wherein the classified layer closest the facing sheet has a weighted average fiber length greater than 2.0 mm. and the classified layer closest the backing sheet has a weighted average fiber length less than 2.0 mm.

10. The disposable diaper of claim 6 wherein the one type of cellulosic fibers is wood pulp.

* * * * *